Figure 1:
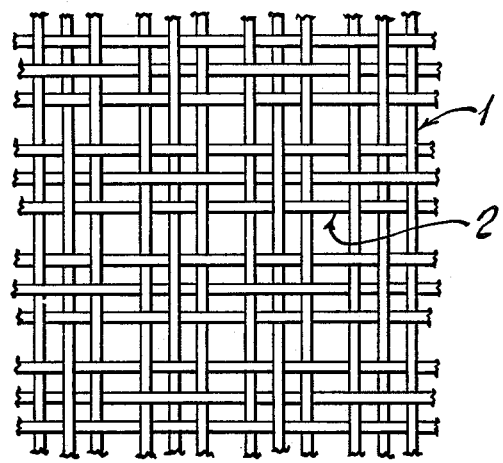

United States Patent [19]

Gianakakos et al.

[11] 4,134,397
[45] Jan. 16, 1979

[54] ORTHOPEDIC BANDAGE

[75] Inventors: Spiros Gianakakos, Highland Park; Neil H. Rosen, Willingboro, both of N.J.; Paul Siminuk, Elkins Park, Pa.

[73] Assignee: Johnson & Johnson, New Brunswick, N.J.

[21] Appl. No.: 802,692

[22] Filed: Jun. 2, 1977

[51] Int. Cl.$^2$ ............................................. A61F 5/04
[52] U.S. Cl. ................................................... 128/90
[58] Field of Search ................. 128/90, 155, 156, 82, 128/83, 82.1

[56] References Cited

U.S. PATENT DOCUMENTS

| | | | |
|---|---|---|---|
| 2,853,067 | 9/1958 | Puharich | 128/90 |
| 3,421,501 | 1/1969 | Beightol | 128/90 |
| 3,669,708 | 6/1972 | Reber et al. | 128/90 |
| 3,683,903 | 8/1972 | Fox et al. | 128/90 |
| 3,686,725 | 8/1972 | Nisbet et al. | 128/90 |
| 3,787,272 | 1/1974 | Nisbet et al. | 128/156 |

*Primary Examiner*—Lawrence W. Trapp
*Attorney, Agent, or Firm*—Robert J. Baran

[57] ABSTRACT

An orthopedic bandage which includes a flexible carrier comprising a woven fiberglass fabric, said fabric being a mock leno weave, and a cast forming composition supported therein comprising a monomer selected from a group consisting of diacetone acrylamide, N isopropyl acrylamide, and mixtures thereof. Preferably said bandage comprises at least nine weight percent diacetone acrylamide.

11 Claims, 2 Drawing Figures

ORTHOPEDIC BANDAGE

FIELD OF INVENTION

An orthopedic bandage which includes a flexible carrier comprising a woven fiberglass fabric, said fabric being a mock leno weave, and a cast forming composition supported thereon comprising a monomer selected from a group consisting of diacetone acrylamide, N isopropyl acrylamide, and mixtures thereof. Preferably said bandage comprises at least nine weight percent diacetone acrylamide and may additionally include other monomers (i.e. other than the aforementioned N-isopropyl acrylamide) which are copolymerizable therewith. Fillers, softeners, etc. as known in the art may also be included in the novel orthopedic bandage of this invention. The bandage is hardened by polymerizing the above monomers by contacting the bandage with water in the presence of a polymerization catalyst such as a redox catalyst system. The bandage may be hardened, for example, by dipping in an aqueous solution, e.g. tap water, containing the catalyst components dissolved therein prior to wrapping the limb of a patient.

BACKGROUND OF THE PRIOR ART

Various materials have been suggested to replace the well known plaster of paris orthopedic bandages that have been almost exclusively used in the preparation of casts for the immobilization and support of parts of the body. Non plaster of paris products which utilize monomers or reactive polymers supported on a carrier, which may be a fabric or foam, have been recently developed in this art. See for Example, U.S. Pat. Nos. 2,853,067; 3,674,021; 3,669,708; 3,656,475; 3,630,194; 3,613,675 and 3,421,501. These products are hardened by means of heat, radiation or chemical catalyzation, to yield a composite structure which generally has the advantage of lighter weight, improved water resistance, improved x-ray transmission, etc. over plaster of paris casts.

The bandage disclosed in U.S. Pat. No. 3,630,194 has been found to have less than desirable initial strength, (hereinafter "green strength"), i.e. it may take as long as one hour to reach acceptable strength at ambient temperature, unless the flexible carrier is a fiberglass fabric, or other low extension, high initial modulus material.

As pointed out in various patents, (see for example U.S. Pat. Nos. 3,787,272; 3,793,686 and 3,686,725) fiber glass fabrics have certain properties which are undesirable in orthopedic bandages. For example, fiberglass fabrics have poor conformability due to the brittleness of the fiber. The patentees suggest that making the fabric from a fiber consisting essentially of very fine, individual filaments having a diameter of no more than 0.00021 inches improves the poor conformability.

The fabrics disclosed in U.S. Pat. Nos. 3,787,272; 3,793,686; and 3,686,725 are knitted fiberglass fabrics. Although these fabrics have adequate conformability, this construction does not give adequate "green strength" with the cast forming composition disclosed in 3,630,194. It is believed that knitted fiberglass fabrics are not suitable for use with said cast forming compositions because of the relatively low $T_g$ of the polymers obtained by polymerizing the monomers defined therein as opposed to the polymers utilized in the other non plaster of paris products of the prior art, e.g. methacrylate polymers.

It has been found that using lighter weight (thinner) woven fiberglass fabrics as the flexible carrier to improve conformability does not provide bandages having adequate "green strength" with the cast forming compositions disclosed in U.S. Pat. No. 3,630,194. It has been found that a certain minimum mass of the flexible carrier is required or it is necessary to wrap the bandage an excessive number of turns around a limb to provide adequate strength during the initial stages of hardening. Additional wrapping is, of course undesirable to the person preparing the cast.

To solve the above noted problems, a woven fiberglass fabric, cut on the bias was used as a carrier for the cast forming monomers described above. This carrier showed some improved conformability after impregnation, and also yielded a product wherein fraying at the edges was reduced as compared to a similar impregnated product based on a straight cut, fiberglass fabric. However, conformability was not as good as desired and the impregnated, bias cut product tended to neck down when being wrapped around the limb of a patient, thus also requiring more turns.

Attempts to improve conformability by using a very open plain or twill weave fiberglass fabric as a carrier were unsuccessful. The fabric could be made but could not be handled without distorting. This fabric, even after impregnation with a monomer or a reactive polymer, quickly became unacceptably distorted when exposed to water to initiate the reaction.

A leno woven fiberglass fabric was also utilized as a carrier, because of its conformability and open weave. Again after impregnation of the fabric with the above defined cast forming composition, the conformability was lost.

The above noted problems are solved by using, as the flexible carrier, the fabric described herein.

SUMMARY OF THE INVENTION

The instant invention relates to a novel orthopedic bandage which has excellent conformability, structural stability, and after hardening provides a high strength, water insensitive, x-ray transparent cast. These desirable properties are provided by the use of a flexible carrier which is a mock leno woven fabric comprising fibers of a low extension, high initial modulus polymer, e.g. fiberglass, to support a cast forming composition comprising a monomer selected from the group consisting of diacetone acrylamide, N-isopropyl acrylamide, and mixtures thereof. For the purposes of this specification, high initial modulus means any polymer having an initial modulus of greater than 5,000,000 lbs./in.$^2$ when measured by the method of ASTM 2256-75.

Mock leno woven fabrics are known in the art and may be generally defined as fabrics wherein groups of three or more warp or filling threads are interlaced in such a way that the threads of each group can come together easily in one bunch, while they are separated from the adjacent groups by reason of the last thread of one group and the first thread of the next group being interlaced in directly opposite order. Such an intersection prevents the two threads from coming together and causes an opening at this point. These fabrics may be made from glass fibers and are well known articles of commerce.

A minimum of bunches of three warp and filling threads are required to produce the mock leno design. Any number of additional threads may be used in the warp and filling groupings. Examples of various mock leno designs possible are described in *Handbook of Weaves* by G. H. Oelsner, Dover Publications, Inc., 1780 Broadway, New York, N.Y., herein incorporated by reference.

The preferred design is groups of three warp yarns to avoid having more than one adjacent fiberglass yarn making the same interlacing pattern with the filling. The inextensible nature of fiberglass tends to cause one or more adjacent warp yarns, that are interlacing alike with the fill yarns, to "pop" up from the surface of the completed fabric. This results in a poor appearance.

Figure 2:
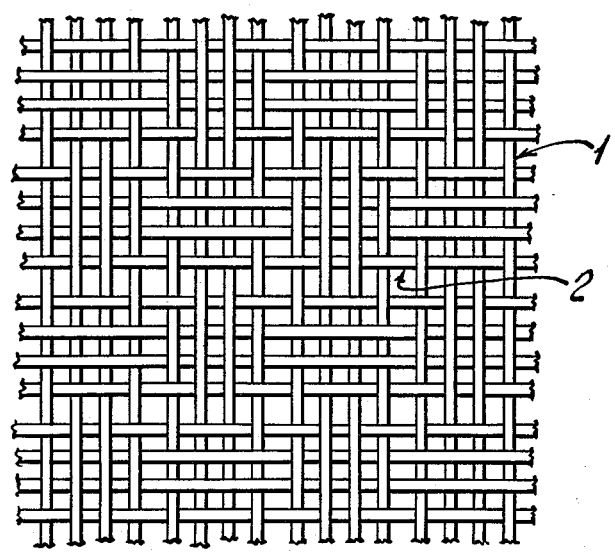

Mock leno fabric structure is shown in FIGS. 1 and 2. FIG. 1 shows a fabric wherein both the warp (1) and the fill (2) threads are grouped in threes and FIG. 2 shows a fabric wherein both the warp (1) and the fill (2) threads are grouped in fours.

The fabric useful in preparing the instant novel orthopedic bandage is characterized as being an open fabric. For example, the fabric will have holes having dimensions of from 0.05" to 0.15" in the warp direction and 0.025" to 0.10" in the fill direction. The fabric may vary in weight from 5.0 to 10.0 ounces per $yard^2$ (oz/yd) perferably from 6.0 to 6.5 oz/yd. The yarn is a multifilament type, wherein the individual filaments may vary in diameter from 0.00015 to 0.00036, preferably about 0.00025 inches; and said yarn may comprise from 50 to 2500 individual filaments. (Fiberglass yarn useful in making the above described fabric is supplied by Owens-Corning Fiberglass Corporation and Pittsburgh Plate Glass. Fiber Glass Division). The fabric may comprise from 20 to 30 ends per inch and from 10 to 18 picks per inch. The yarn may be twisted, e.g. from 0.5 to 1.0 twists per inch. Some twist in the yarn is desirable to aid in the weaving operations. Minimum twist compatible with easy fabrication is desirable to preserve the conformability of the final impregnated product. For this reason, 0.5-1.0 twists per inch are preferred although yarns may be utilized with any number of twists per inch that is practical. Commercially prepared plied yarns can be used as well as specially prepared plied yarns to achieve yarn sizes that are not offered by the fiberglass multifilament yarn manufacturers. It is preferred, however, to utilize single yarns to avoid ply twist that interferes with fabric conformability.

Balanced fabrics (fabrics with the same size yarns in warp and filling) are preferred to achieve equal reinforcement in the final product in both directions. Any manner of unbalanced design, however, may be utilized.

Yarns other than fiberglass may be used which have similar high initial modulus and elongation properties. An example is Kevlar yarn supplied by E. I. duPont DeNemours which is of the Aramid family (a manufactured fiber in which the fiber forming substance is a long chain synthetic polyamide in which at least 85% of the amid linkages are attached directly to two aromatic rings). Fiberglass is the preferred material due to supply and cost considerations.

The cast forming composition, the method of applying it to a flexible carrier and the method of using the resulting orthopedic bandage is described in U.S. Pat. No. 3,630,194, herein incorporated by reference. Of course, the flexible carrier used in making the orthopedic bandages of the instant invention will be the above described mock leno weave fabric preferably a fiberglass fabric.

For example, the mock leno wove, fiberglass fabric is impregnated with the cast forming composition from a suitable solvent, a melt or the cast forming composition is powdered onto the fabric in admixture with other monomers co-polymerizable therewith, the polymerization catalysts, the fillers or polymers (as described in U.S. Pat. No. 3,630,194), or any of the aforesaid may be impregnated or powdered onto the fabric in a serial manner.

Of the solids added to the fabric, the total amount of monomer components may comprise from 30 to 100% of the total weight. Preferably the monomer components will comprise from 50 to 80% weight of the total add on with the fillers comprising the remainder.

When the polymerization catalyst is the conventional redox initiator described in U.S. Pat. No. 3,630,194 both the oxidizing and reducing agents may be added to the fabric, however, moisture must be excluded from contact with the bandage both during preparation and storage, otherwise prehardening of the bandage may occur.

Suitable solvents for use in impregnating the fabric with the cast forming composition are described in U.S. Pat. No. 3,630,194. Suitable methods of impregnating and drying are also disclosed therein. Finally, methods of packaging the dried, impregnated bandage are disclosed, which avoid the above mentioned problem of moisture caused prehardening.

Prior to applying the cast forming composition to said mock leno weave fiberglass fabric, it is desirable to heat treat the fabric by burning, in air, at temperatures of from 300° C. to 550° C. to remove residual products remaining on the fabric after the construction thereof. For example, warp sizes, etc. should be removed by heat treating. The heat treated fabric may then be impregnated with an aqueous solution of a silane, such as γ-methacryloxy propyltrimethoxysilane, or γ-aminopropyl-triethoxysilane or glycidoxypropyltrimethoxysilane, etc. and dried. The resulting fabric thus contains a silane finish which facilitates bonding of the cast forming composition to the fabric. As disclosed in U.S. Pat. No. 3,630,194 additional adhesives may be used to bond the cast forming composition to the fabric.

Now having described the instant invention generally and in detail, the following examples are offered to further illustrate this invention. However, there is no intent to be limited to the specific embodiments disclosed in these examples.

EXAMPLE I

A six leaf, mock leno weave fiberglass fabric modified by the addition of a warp yarn weaving plain between groups of three (3) warp ends in the mock leno configuration was prepared. This fabric was heat cleaned at 1000° F. for forty-five (45) minutes and treated with an aqueous 1.0% by weight solution of Union Carbide A 174 silane, (γ-methacryloxy propyltrimethoxy). The silane finish was added to the fabric by dipping into a solution of 20 mls. of silane added to 2 liters of water. The fabric was dipped into the solution for ten seconds and air dried after allowing the excess solution to drip off the fabric. A mono-molecular layer of silane on the fiberglass fabric is desirable, therefore, the weight of the fiberglass to be used with the solution is not critical and the solution may be used until exhaustion. The amount of the melt picked up by the fabric was 59 weight percent based on the fabric. A cast forming composition consisting of the following was then applied from a melt:

975 grams Diacetone acrylamide
20 grams Carbowax 4000 (Union Carbide's Polyethylene Oxide)
36.3 grams glycerin
13.6 grams propylene glycol
25.3 grams Carboxymethyl cellulose The cast forming composition was heated to a temperature from about 60° C. to 62° C. which was sufficient to melt the mixture without causing degradation of any of the components. Bandages of 2½" × 90" were rolled and dipped in 500 ml. water, at a temperature of about 24° C., which contained the following catalyst formulation:

20 grams ammonium persulfate
20 grams sodium persulfite
14 grams sodium bicarbonate The bandages were then wrapped on a 2¾" dowel and the crush strengths for a 1½ cm. cast deflection after a ten minute cure at room temperature are listed below:

| Bandage # | Lbs. of Crush Strength |
|---|---|
| 1 | 72.5 |
| 2 | 62.5 |
| 3 | 57.5 |
| 4 | 86.0 |
| 5 | 82.5 |

The crush strength was measured by use of a test machine available from John Chatillon and Sons, New York, N.Y. Model UTSM, having a 0–250 lb. gage, in 2.5 lb. graduations. The test speed was 15" per minute. The values obtained are comparable to those obtained from plain weave control fabrics. It was determined subjectively in wrapping evaluation on an arm that the mock leno design had superior conformability and aesthetic characteristics to plain weave fiberglass fabrics.

EXAMPLE II

The bandage described in Example I was wrapped on a forearm. Wrapping a limb is analogous to wrapping a cone shape. When a cone shape is wrapped with a tape material, gaps will appear between the tape being wrapped and the previous layer as wrapping proceeds from the large diameter to the smaller diameter of the cone.

Gaps occur when wrapping plaster bandages on limbs but they are removed by folding the material or "tucking" the bandage. The light weight and lack of resilience of the cotton gauze in plaster bandages combined with the heavy weight of plaster used causes a minimum of surface disturbance in the cast in these folded over areas.

When wrapping with closed, plain weave fiberglass fabrics, the gaps that occur on the interior of the cast must be folded over by subsequent layers and noticeable lumps form at these points. These are sources for pressure on the skin which may lead to skin damage. The resilience of the fiberglass fabric and lack of monomer tackiness causes gaps to remain on the surface of the final wrap since the fabric will not remain folded over. This results in a poor surface appearance.

With a mock leno based fiberglass bandage, however, it is not necessary to fold over or "tuck" the bandage while wrapping. The openness of the weave will allow the bandage to distort sufficiently to remove the gaps as they are formed. Lumps are not formed on the interior of the cast and the cast surface appearance is acceptable.

What is claimed:

1. An orthopedic bandage which includes a flexible carrier comprising a woven fabric, said fabric being characterized as a mock leno weave, which is formed from a yarn having an initial modulus of greater than 5,000,000 lbs./in.$^2$, and a cast forming composition supported thereon, said cast forming composition comprising a monomer selected from the group consisting of diacetone acrylamide, n isopropyl acrylamide and mixtures thereof.

2. An orthopedic bandage according to claim 1 wherein said fabric is a fiberglass fabric.

3. An orthopedic bandage according to claim 2 wherein said fabric is characterized as having groups of three or more warp or filling threads interlaced in such a way that the threads of each group can come together easily in one bunch, while they are separated from the adjacent groups by reason of the last thread of one group and the first thread of the next group being interlaced in directly opposite order.

4. An orthopedic bandage according to claim 3 wherein said fabric is characterized as having groups of three warp yarns.

5. An orthopedic bandage according to claim 4 wherein said fabric is characterized as being an open fabric having holes in dimensions of from 0.05 to 0.15 inches in the warp direction and from 0.025 inches to 0.10 inches in the fill direction.

6. An orthopedic bandage according to claim 5 wherein the yarn is a multi-filament type yarn wherein the individual filaments vary in diameter from 0.00015 to 0.00036 and said yarn comprises from 50 to 2500 individual filaments.

7. An orthopedic bandage according to claim 6 wherein the fabric comprises from 20 to 30 ends per inch and from 10 to 18 picks per inch.

8. An orthopedic bandage according to claim 7 wherein the yarn has a twist of from 0.5 to 1.0 twists per inch.

9. An orthopedic bandage according to claim 1 wherein the total amount of monomer components comprises from 30 to 100 percent of the total weight of said fabric.

10. An orthopedic bandage according to claim 9 wherein said monomer is diacetone acrylamide.

11. An orthopedic bandage according to claim 1 wherein said diacetone acrylamide comprises at least nine weight percent of said bandage.

* * * * *